United States Patent
Pahan

(10) Patent No.: US 9,968,582 B2
(45) Date of Patent: May 15, 2018

(54) USE OF A BENZOATE CONTAINING COMPOSITION IN UREA CYCLE DISORDERS AND NEURODEGENERATIVE DISORDERS

(71) Applicant: Rush University Medical Center, Chicago, IL (US)

(72) Inventor: Kalipada Pahan, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 0 days. days.

(21) Appl. No.: 15/110,702

(22) PCT Filed: Jan. 16, 2015

(86) PCT No.: PCT/US2015/011798
§ 371 (c)(1),
(2) Date: Jul. 8, 2016

(87) PCT Pub. No.: WO2015/109215
PCT Pub. Date: Jul. 23, 2015

(65) Prior Publication Data
US 2016/0331714 A1  Nov. 17, 2016

Related U.S. Application Data

(60) Provisional application No. 61/928,622, filed on Jan. 17, 2014.

(51) Int. Cl.
*A61K 31/235* (2006.01)
*A23L 33/10* (2016.01)
*A61K 9/00* (2006.01)

(52) U.S. Cl.
CPC ........... *A61K 31/235* (2013.01); *A23L 33/10* (2016.08); *A61K 9/0053* (2013.01)

(58) Field of Classification Search
CPC .................................................. A61K 31/235
USPC ......................................................... 514/533
See application file for complete search history.

(56) References Cited

U.S. PATENT DOCUMENTS 4,284,647 A     8/1981  Brusilow et al.
2008/0171792 A1  7/2008  Jobdevairakkam et al.

OTHER PUBLICATIONS

Khasanavis and Pahan, J Neuroimmune Pharmacology (2012), vol. 7(2), pp. 424-435.*
Jana, Arundhati, K.K. Modi, A. Roy, J.A. Anderson, R.B. van Breemen, and K. Pahan, "Up-regulation of neurotrophic factors by cinnamon and its metabolite sodium benzoate: Therapeutic implications for neurodegenerative disorders," Journal of Neuroimmune Pharmacology (Jun. 2013), vol. 8, No. 3, p. 1-26. (Year: 2013).*
International Search Report and Written Opinion for related International Application No. PCT/US2015/011798, dated Jun. 23, 2015 (9 pages).

(Continued)

Primary Examiner — Craig D Ricci
Assistant Examiner — Janet L. Coppins
(74) Attorney, Agent, or Firm — Eric D. Babych; Brinks Gilson & Lione

(57) ABSTRACT

This disclosure relates to pharmaceutical compositions useful for inhibiting the progression of urea cycle disorders and neurodegenerative disorders, such as Parkinson's disease, Alzheimer's disease, and multiple sclerosis. The pharmaceutical compositions may include glyceryl tribenzoate and glyceryl dibenzoate. The pharmaceutical compositions may be orally administered to the patient one time per day.

15 Claims, 18 Drawing Sheets

(56) References Cited

OTHER PUBLICATIONS

Lambert, D.M., "Rationale and applications of lipids as prodrug carriers," European Journal of Pharmaceutical Sciences, 11 Suppl. 2 (2000) S15-S27.

Adams, T.B, S.M. Cohen, J. Doull, V.J. Feron, J.I. Goodman, L.J. Marnett, I.C. Munro, P.S. Portoghese, R.L. Smith, W.J. Waddell, and B.M. Wagner, "The FEMA GRAS assessment of benzyl derivatives used as flavor ingredients," Food and Chemical Toxicology (2005), vol. 43, pp. 1207-1240.

Breitkreutz, Jörg, F. El-Saleh, C. Kiera, P. Kleinebudde, and W. Wiedey, "Pediatric drug formulations of sodium benzoate: II. Coated granules with a lipophilic binder," European Journal of Pharmaceutics and Biopharmaceutics (2003), vol. 56, pp. 255-260.

Cederbaum, Stephen, C. LeMons, and M.L. Batshaw, "Alternative pathway or diversion therapy for urea cycle disorders now and in the future," Molecular Genetics and Metabolism (2010), vol. 100, pp. 219-220.

Jana, Arundhati, K.K. Modi, A. Roy, J.A. Anderson, R.B. van Breemen, and K. Pahan, "Up-regulation of neurotrophic factors by cinnamon and its metabolite sodium benzoate: Therapeutic implications for neurodegenerative disorders," Journal of Neuroimmune Pharmacology (Jun. 2013), vol. 8, No. 3, 26 pages.

Pahan, Kalipada, "Immunomodulation of experimental allergic encephalomyelitis by cinnamon metabolite sodium benzoate," Immunopharmacology & Immunotoxicology (Dec. 2011), vol. 33, No. 4, 13 pages.

\* cited by examiner

Control     EAE     EAE + GTB    EAE + Vehicle

FIG. 3B                                                 Spinal Cord

FIG. 4D
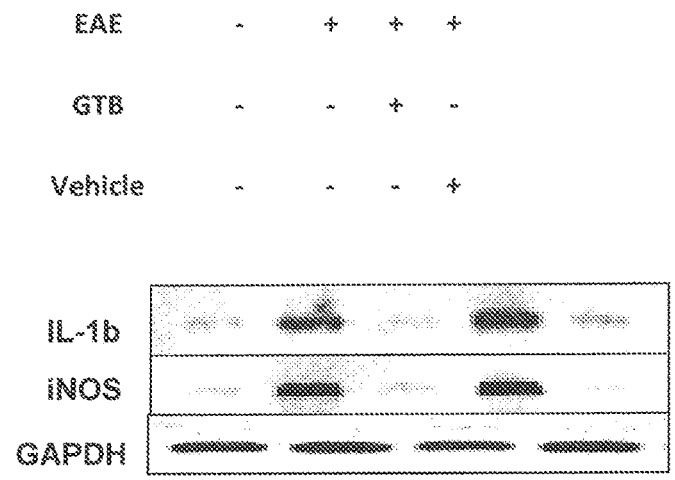
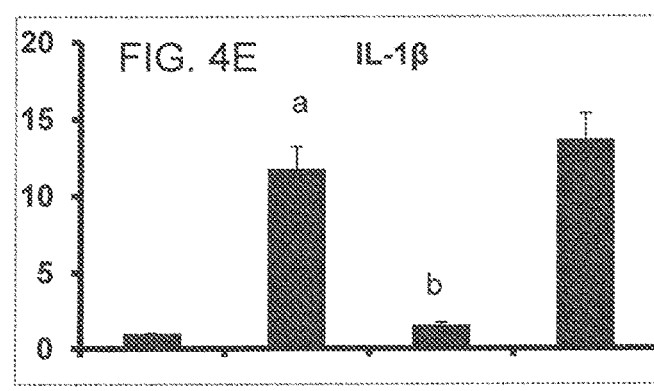
FIG. 4E
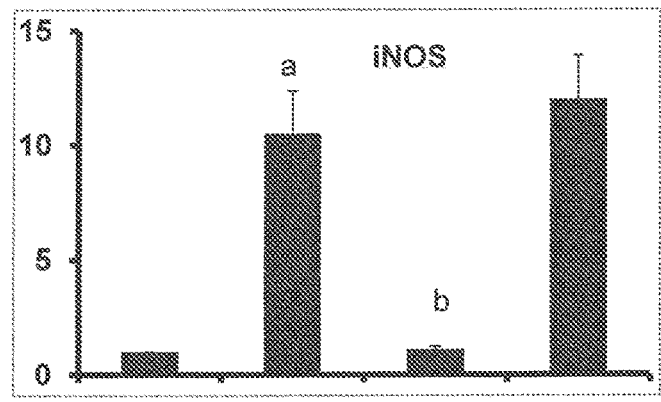
FIG. 4F

FIG. 5D
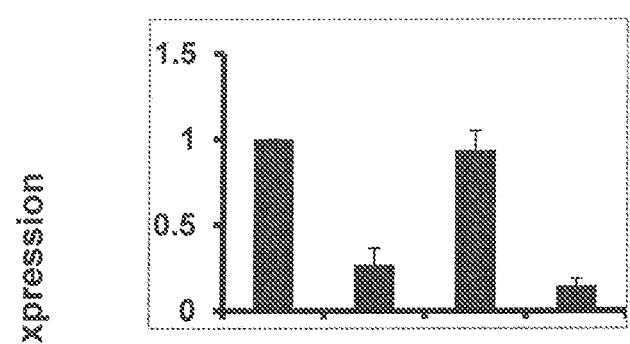
MBP
a  b
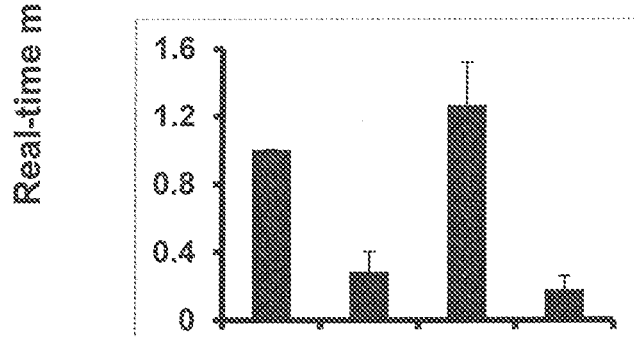
a  b
PLP
FIG. 5E

USE OF A BENZOATE CONTAINING COMPOSITION IN UREA CYCLE DISORDERS AND NEURODEGENERATIVE DISORDERS

CROSS-REFERENCE TO RELATED APPLICATIONS

The present application claims the benefit of U.S. Provisional Patent Application No. 61/928,622, filed Jan. 17, 2014, the contents of which are incorporated into the present application in their entirety.

BACKGROUND

1. Field of the Invention

The present disclosure generally relates to pharmaceutical compositions useful for the treatment of diseases and disorders. More particularly, the disclosure relates to pharmaceutical compositions comprising glyceryl tribenzoate and/or glyceryl dibenzoate for the treatment of urea cycle disorders and neurodegenerative disorders.

2. Description of the Related Art

Cinnamon, the brown bark of cinnamon tree, is a commonly used spice and flavoring material for desert, candies, chocolate etc. It has a long history of being used as medicine as well. Medieval physicians used cinnamon in medicines to treat a variety of disorders, including arthritis, coughing, hoarseness, sore throats, etc. In addition to containing manganese, dietary fiber, iron, and calcium, cinnamon contains three major compounds—cinnamaldehyde, cinnamyl acetate and cinnamyl alcohol. After intake, these three active compounds are converted into cinnamic acid by oxidation and hydrolysis, respectively. Then, cinnamic acid is β-oxidized to benzoate in the liver. This benzoate exists as sodium salt (sodium benzoate) or benzoyl-CoA.

Sodium benzoate is a widely-used food preservative due to its anti-microbial properties. It also has medical importance as a component of Ucephan™, a Food and Drug Administration (FDA)-approved drug used in the treatment for hepatic metabolic defects associated with hyperammonemia, such as urea cycle disorder. The present inventor explored a novel use of sodium benzoate in treating the disease process of relapsing-remitting EAE in female SJL/J mice (see Brahmachari and Pahan, "Sodium benzoate, a food additive and a metabolite of cinnamon, modifies T cells at multiple steps and inhibits adoptive transfer of experimental allergic encephalomyelitis," J. Immunol., 2007, Jul. 1; 179(1):275-83, the entire contents of which are expressly incorporated into the present application by reference).

The present inventor also discovered that sodium benzoate suppresses the disease process of multiple sclerosis (MS) in mice. The inventor has also discovered that sodium benzoate up-regulates a protein called DJ-1, which is a beneficial, neuroprotective protein having implications in neurodegenerative disorders, such as Parkinson's disease (PD) and Alzheimer's disease (AD) (see Khasnavis and Pahan, "Sodium Benzoate, a Metabolite of Cinnamon and a Food Additive, Upregulates Neuroprotective Parkinson Disease Protein DJ-1 in Astrocytes and Neurons," Journal of Neuroimmune Pharmacology, June 2012, Volume 7, Issue 2, pp 424-435, the entire contents of which are expressly incorporated into the present application by reference).

Further, it has been found that the level of neurotrophic factors, such as brain-derived neurotrophic factor (BDNF) and neurotrophin-3 (NT-3), decreases in the brain of patients with different neurodegenerative disorders, such as AD and PD. Recently, the present inventor delineated that sodium benzoate increases the production of BDNF and NT-3 in brain cells, indicating that it could be beneficial for neurodegenerative disorders (see Jana et al., "Up-regulation of neurotrophic factors by cinnamon and its metabolite sodium benzoate: therapeutic implications for neurodegenerative disorders," J. Neuroimmune Pharmacol., 2013 June; 8(3): 739-55, the entire contents of which are expressly incorporated into the present application by reference).

However, sodium benzoate is quickly metabolized and excreted from the body. Therefore, sodium benzoate is generally administered three to four times per day, at least in connection with urea cycle disorders, in order to ensure continual removal of toxic ammonia from the bloodstream.

BRIEF SUMMARY

The present disclosure relates to compositions and methods for the treatment of urea cycle disorders and neurodegenerative disorders. In one aspect, a method for inhibiting the progression of a urea cycle disorder is disclosed. The method comprises administering to a patient in need thereof an effective amount of a pharmaceutical composition comprising glyceryl tribenzoate and/or glyceryl dibenzoate.

In another aspect, a method for inhibiting the progression of a neurodegenerative disorder is provided. The method comprises administering to a patient in need thereof an effective amount of a pharmaceutical composition comprising glyceryl tribenzoate and/or glyceryl dibenzoate.

The present disclosure also relates to the manufacture of medicaments. In one aspect, the present disclosure relates to the use of a glyceryl tribenzoate and/or a glyceryl dibenzoate compound for the manufacture of a medicament for the treatment of a urea cycle disorder.

In another aspect, the present disclosure relates to the use of a glyceryl tribenzoate and/or a glyceryl dibenzoate compound for the manufacture of a medicament for the treatment of a neurodegenerative disorder.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

FIGS. 3A-3C depict infra-red scans of the brain and spinal cord of test mice.

FIGS. 4D-4F depict data indicating a marked expression of pro-inflammatory molecules like iNOS and IL-1β in the spinal cord of untreated EAE mice compared to control mice and also indicating that GTB treatment dramatically reduced the expression of these pro-inflammatory molecules in the spinal cord of EAE mice.

FIGS. 5C-5E relate to the monitoring of the expression of three myelin genes, myelin basic protein (MBP) and proteolipid protein (PLP), and indicate a marked loss of mRNA expression of these genes in the spinal cord of untreated EAE mice compared to control mice. The figures also depict a significant restoration of myelin gene mRNA expression in the spinal cord of EAE mice that were treated with GTB but not vehicle.

DETAILED DESCRIPTION

Figure 1A:
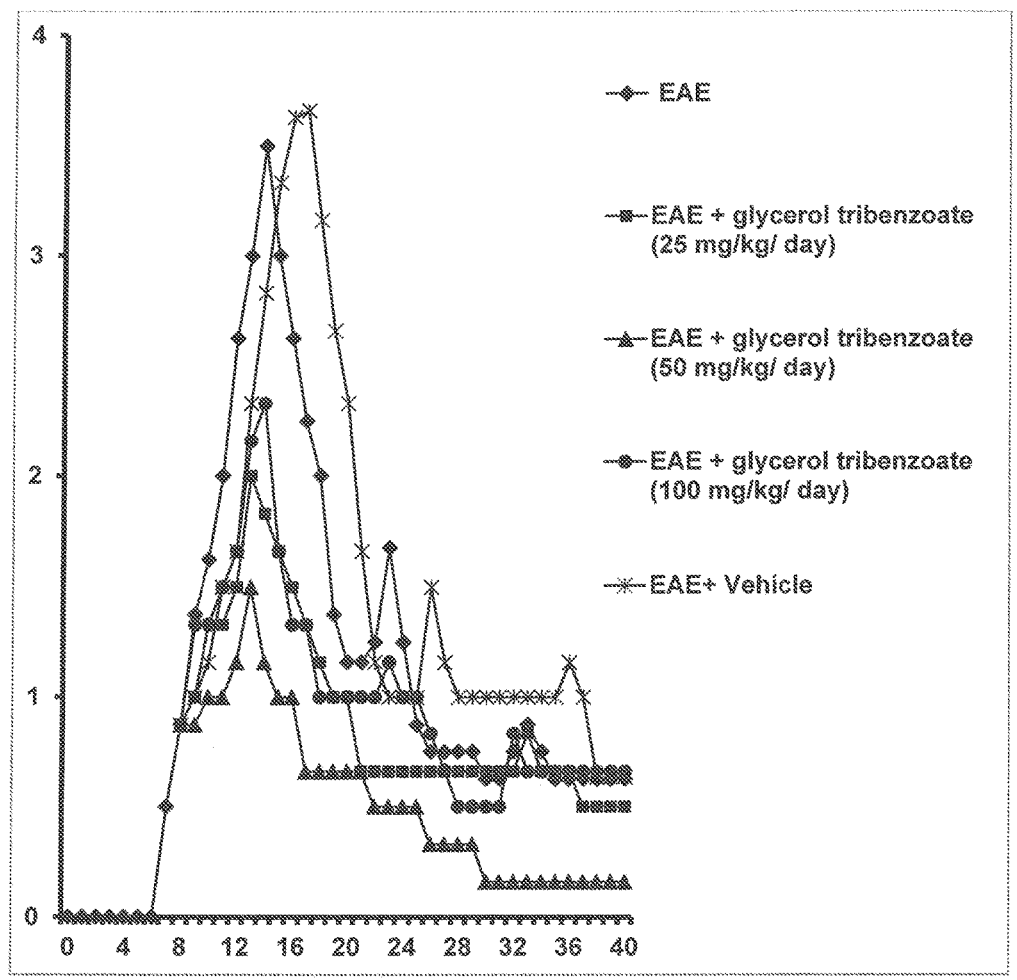
FIGS. 1A-1C depict a graphical analysis of the inhibitory effect of glycerol tribenzoate in connection with Experimental Allergic Encephalomyelitis (EAE).

Various embodiments are described below. The relationship and functioning of the various elements of the embodiments may better be understood by reference to the following detailed description. However, embodiments are not limited to those explicitly disclosed herein. It should be understood that in certain instances, details may have been omitted that are not necessary for an understanding of embodiments disclosed herein.

Although sodium benzoate exhibits beneficial effects in connection with urea cycle disorders, MS, PD, AD, and other neurodegenerative disorders, the fact that the sodium benzoate is quickly metabolized and excreted from the body poses certain problems that can only be addressed by repeatedly administering this compound to patients, generally about three to four times per day. Therefore, a slow-release form of sodium benzoate that allows for a reduced administration regime and improved patient compliance would be beneficial.

The present disclosure addresses this issue by providing a novel treatment for urea cycle disorders and neurodegenerative disorders that requires only a single daily administration of a pharmaceutical composition. In some aspects, the treatment for the urea cycle disorders and neurodegenerative disorders may include a twice daily administration of a pharmaceutical composition. In certain aspects, the pharmaceutical composition disclosed herein comprises glyceryl tribenzoate (also known as tribenzoin). In other aspects, the pharmaceutical composition disclosed herein comprises glyceryl dibenzoate. In some aspects, the pharmaceutical composition comprises both glyceryl tribenzoate and glyceryl dibenzoate. Glyceryl di- and tribenzoate will slowly form sodium benzoate in the body since these molecules will be cleaved in the intestine by various lipases. Therefore, it is hypothesized that glyceryl di- and tribenzoate will exhibit much improved therapeutic efficacies as compared to sodium benzoate.

In one aspect of the present disclosure, a treatment is disclosed for inhibiting the progression of urea cycle disorders. A urea cycle disorder is a genetic disorder caused by a deficiency of one of the enzymes in the urea cycle that is responsible for removing ammonia from the blood stream. There are six know disorders of the urea cycle. Each can be classified by the initials of the missing enzyme. Thus, the six known urea disorders may be referred to as N-acetylglutamate synthase (NAGS), Carbamoyl Phosphate Synthetase 1 (CPS1), Ornithine transcarbamoylase (OTC), Argininosuccinate synthase (ASS), argininosuccinate lyase (ASL), and Arginase 1 (ARG1). The treatment comprises administering an effective amount of a pharmaceutical composition comprising glyceryl tribenzoate and/or glyceryl dibenzoate to a patient in need thereof. In accordance with the present disclosure, the treatment may be administered one time per day. In some aspects, the treatment may include a twice daily administration.

In another aspect of the present disclosure, a treatment is disclosed for inhibiting the progression of neurodegenerative disorders. The treatment comprises administering an effective amount of a pharmaceutical composition comprising glyceryl tribenzoate and/or glyceryl dibenzoate to a patient in need thereof. In some aspects, the neurodegenerative disorders are selected from the group consisting of PD, AD, MS, depression, Huntington's Disease, dementia, and any memory loss disorder. In some aspects, the neurodegenerative disorders may be identified by a decrease in levels of BDNF or NT-3 relative to normal subjects. In accordance with the present disclosure, the treatment may be administered one time per day. In some aspects, the treatment may include a twice daily administration.

In the treatment methods contemplated by the present disclosure, the glyceryl tribenzoate and/or glyceryl dibenzoate may be used alone or in compositions together with a pharmaceutically acceptable carrier or excipient. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other suitable pharmaceutically acceptable excipients are described in "Remington's Pharmaceutical Sciences," Mack Pub. Co., New Jersey, 1991, the contents of which are expressly incorporated herein by reference.

In certain embodiments, the glyceryl tribenzoate and/or glyceryl dibenzoate may be orally administered to humans and other animals. The glyceryl tribenzoate and/or glyceryl dibenzoate may be formulated for administration and methods of formulation are well known in the art (see, for example, Remington: *The Science and Practice of Pharmacy*, Mack Publishing Company, Easton, Pa., 19th Edition (1995)). Pharmaceutical compositions for use in accordance with the present disclosure can be in the form of sterile, non-pyrogenic liquid solutions or suspensions, coated capsules, lyophilized powders, or other forms known in the art.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Effective amounts of the compositions of this disclosure generally include any amount sufficient to inhibit (e.g. slow or stop) the progression of a disorder, such as urea cycle disorders and neurodegenerative disorders. The amount of active ingredient (glyceryl tribenzoate and/or glyceryl dibenzoate) that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disorder or disease undergoing therapy. The therapeutically effective amount for a given situation can be readily determined by routine experimentation and is within the skill and judgment of the ordinary clinician.

According to the methods of treatment of the present disclosure, progression of the disorder is slowed or stopped in a patient, such as a human or lower mammal, by administering to the patient an effective amount of the glyceryl tribenzoate and/or glyceryl dibenzoate in such amounts, and for such time as is necessary, to achieve the desired result. An amount of a compound that is effective to slow or stop the progression of a disease or disorder may refer to a sufficient amount of the compound to treat the disease or disorder at a reasonable benefit/risk ratio applicable to any medical treatment.

It will be understood, however, that the total daily usage of the compounds and compositions of the present disclosure will be decided by the attending physician within the scope of sound medical judgment. The specific therapeutically effective dose level for any particular patient will depend upon a variety of factors including the disease or disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The "effective amount" or dose of a compound of the present disclosure, such as glyceryl tribenzoate and/or glyceryl dibenzoate, to be administered to warm-blooded animals, such as humans, may vary depending upon the disorder to be treated. In connection with urea cycle disorders, in certain aspects of this disclosure, the effective amount may be from approximately 3 g to approximately 10 g per 50 kg person, per day, or any amount or sub-range thereof. For example, the effective amount may be about 4 g, about 5 g, about 6 g, about 7 g, about 8 g, or about 9 g. In some aspects, the dose may be from approximately 3 g to approximately 6 g, per 50 kg person, per day. In other aspects, the effective amount may be from about 100 mg/kg to about 200 mg/kg, per person, per day. In connection with neurodegenerative disorders, in certain aspects of this disclosure, the effective amount may be from approximately 1 g to approximately 5 g per 50 kg person, per day, or any amount or sub-range thereof. For example, the effective amount may be about 2 g, about 3 g, or about 4 g. In some aspects, the dose may be from approximately 1 g to approximately 3 g, per 50 kg person, per day. In one particular aspect, the dose may be about 1.25 g per 50 kg person, per day. In other aspects, the effective amount may be from about 25 mg/kg to about 50 mg/kg, per person, per day.

EXAMPLES

The following experiments have been (or will be) conducted to test the efficacy of glyceryl tribenzoate (tribenzoin) and/or glyceryl dibenzoate in the treatment of MS, PD and urea cycle disorders. The examples set forth below illustrate the experiments using glyceryl tribenzoate. Similar experiments will be conducted using glyceryl dibenzoate or combinations of glyceryl tribenzoate and glyceryl dibenzoate.

Adoptively-Transferred Experimental Allergic Encephalomyelitis (EAE).

Figure 1B:
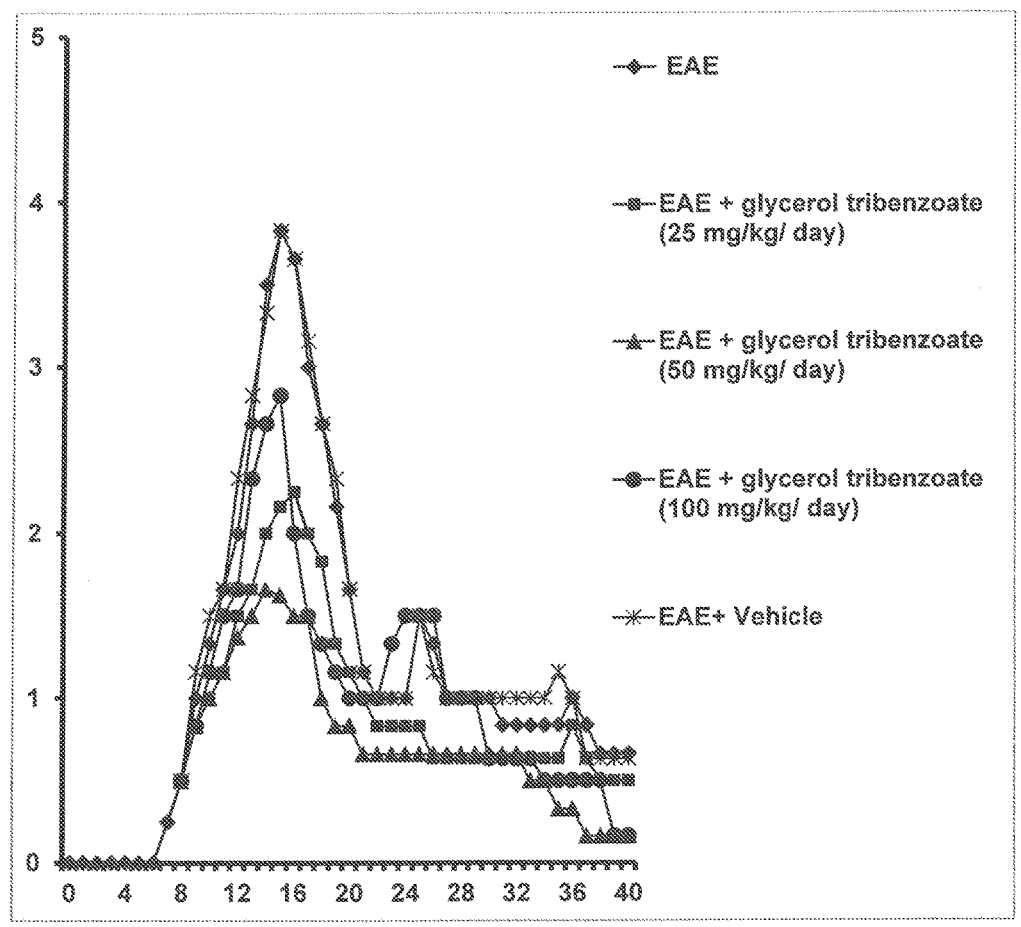
Figure 1C:
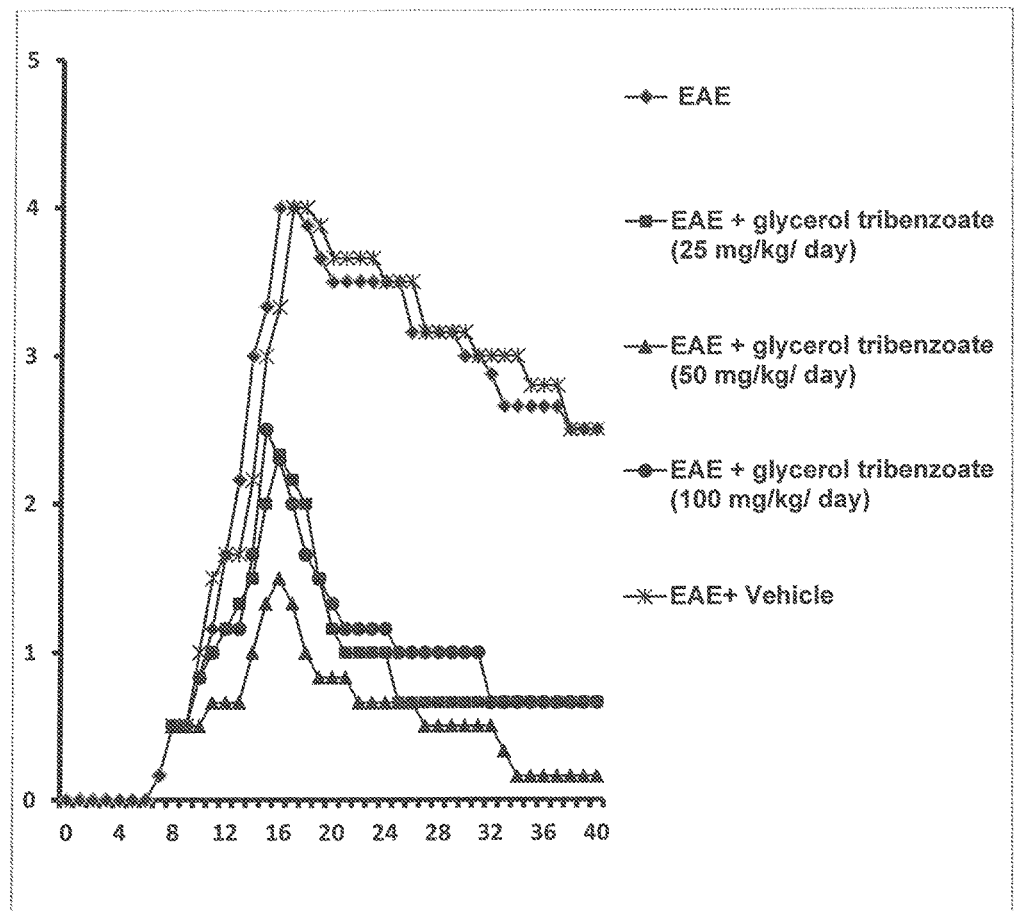
Figure 2:
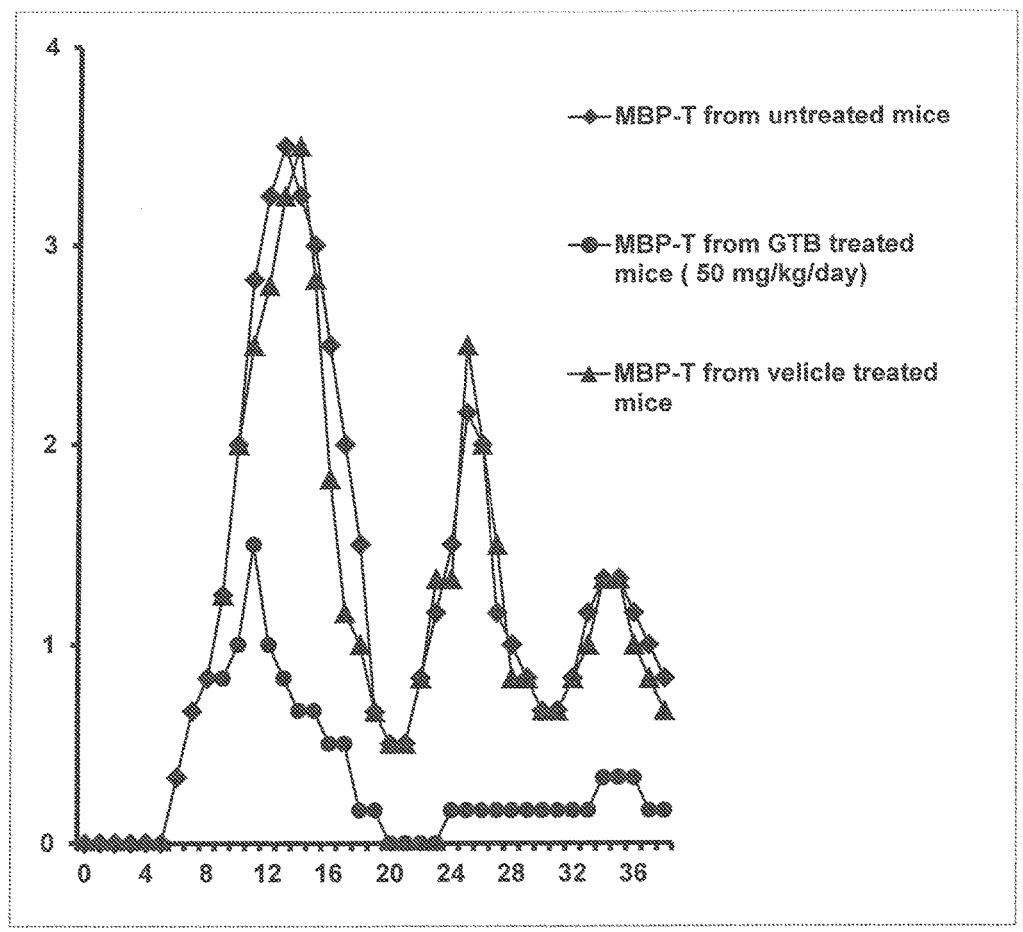
FIG. 2 depicts data showing that mice receiving MBP-primed T cells from GTB-treated donor mice exhibited significantly reduced clinical symptoms and disease severity compared to mice receiving MBP-primed T cells from either untreated donor mice or vehicle-treated donor mice.

Female SJL/J mice (4-5 weeks old) were purchased from Harlan Sprague-Dawley (Indianapolis, Ind.). Donor mice were immunized s.c. with 400 μg bovine Myelin Basic Protein (MBP) and 60 μg M. tuberculosis in Incomplete Freund's Adjuvant (IFA). Animals were killed 10-12 days post-immunization, and the draining lymph nodes were harvested and single cell suspensions were cultured in RPMI 1640 supplemented with 10% Fetal Bovine Serum (FBS), 50 μg/mL MBP, 50 μM 2-ME, 2 mM L-glutamine, 100 U/mL penicillin, and 100 μg/ml streptomycin. On day 4, cells were harvested and re-suspended in Hank's balanced salt solution (HBSS). A total of $2 \times 10^7$ viable cells in a volume of 200 μL were injected into the tail vein of naive mice. Pertussis toxin (150 ng/mouse; Sigma-Aldrich) was injected once via i.p. route on 0 day post-transfer (dpt) of cells. Animals were observed daily for clinical symptoms. Six mice were used in each group. Female mice (4-5 week old) were randomly selected for any group. Experimental animals were scored by a masked investigator, as follows: 0, no clinical disease; 0.5, piloerection; 1, tail weakness; 1.5, tail paralysis; 2, hind limb weakness; 3, hind limb paralysis; 3.5, forelimb weakness; 4, forelimb paralysis; 5, moribund or death. In FIGS. 1A and 2, the y-axis is mean clinical score and the x-axis is days post-transfer. In FIG. 1B-1C, the y-axis is mean clinical score and the x-axis is days post-immunization.

Relapsing EAE in 5B6 PLP-TCR Tg Mice.

$PLP_{139-151}$-specific 5B6 TCR Tg mice were obtained from Prof. Vijay Kuchroo (Harvard Medical School, Boston, Mass.). Female Tg mice (4-5 weeks old) were immunized with 10 or 25 μg of PLP139-151 in M. tuberculosis in IFA as described above. Mice also received pertussis toxin (150 ng/mouse) once on 0 day post-immunization (dpi). In the EAE group (FIG. 1B), where female PLP-TCR transgenic mice were immunized with 25 μg PLP139-151, two mice died without humane intervention on 17 days post-immunization (dpi) and four moribund mice were decapitated after anesthesia. However, according to the disease scale, all six mice in this group received a score of 5.

Chronic EAE.

C57BL/6 mice were immunized with 100 μg of MOG35-55 as described above. Mice also received two doses of pertussis toxin (150 ng/mouse) on 0 and 2 dpi.

Glyceryl Tribenzoate (GTB) Treatment.

GTB was mixed in 0.5% methylcellulose (MC) and EAE mice were gavaged 100 μL GTB-mixed MC once daily using gavage needle. Therefore, control EAE mice received only MC as vehicle.

Histological Microscopy.

On 14 dpi (first chronic phase), five mice from each of the following groups (control, EAE, EAE+GTB, and EAE+vehicle) were anesthetized. After perfusion with phosphate buffered saline (PBS) (pH 7.4) and then with 4% (w/v) paraformaldehyde solution in PBS, cerebellum and whole spinal cord was dissected out from each mouse. The tissues were further fixed and then divided into halves: one-half was used for histological staining whereas the other half was used for myelin staining. For histological analysis, routine histology was performed to obtain perivascular cuffing and morphological details of CNS tissues of EAE mice. Paraformaldehyde-fixed tissues were embedded in paraffin, and serial sections (4 μm) were cut. Sections were stained with conventional H&E staining method. Digital images were collected under bright-field setting using an ×40 objective. Slides were assessed in a blinded fashion by three examiners for inflammation in different anatomical compartments (meninges and parenchyma). Inflammation was scored using the following scale as described: for meninges and parenchyma: 0, no infiltrating cells; 1, few infiltrating cells; 2, numerous infiltrating cells; and 3, widespread infiltration. For vessels: 0, no cuffed vessel; 1, one or two cuffed vessels per section; 2, three to five cuffed vessels per section and 3, more than five cuffed vessels per section. At least six serial sections of each spinal cord from each of five mice per group were scored and statistically analyzed by ANOVA.

Staining for Myelin.

Sections were stained with Luxol fast blue for myelin as described earlier. Slides were assessed in a blinded fashion for demyelination by three examiners using the following scale: 0, normal white matter; 1, rare foci; 2, a few areas of demyelination; and 3, large areas of demyelination. At least six serial sections of each spinal cord from each of five mice per group were scored and statistically analyzed by ANOVA.

Semi-Quantitative RT-PCR Analysis.

Total RNA was isolated from splenic T cells and spinal cord by using the RNeasy mini kit (Qiagen, Valencia, Calif.) and from spleen and cerebellum by using the Ultraspec-II RNA reagent (Biotecx laboratories, Inc, Houston, Tex.) following manufacturer's protocol. To remove any contaminating genomic DNA, total RNA was digested with DNase. Semi-quantitative RT-PCR was carried out using a RT-PCR kit from Clonetech (Mountain View, Calif.). Briefly, 1 μg of total RNA was reverse transcribed using oligo$(dT)_{12-18}$ as primer and MMLV reverse transcriptase (Clontech) in a 20 μL reaction mixture. The resulting cDNA was appropriately-diluted, and diluted cDNA was amplified using Titanium Taq DNA polymerase and following primers. Amplified products were electrophoresed on a 1.8% agarose gels and visualized by ethidium bromide staining.

```
(SEQ ID NO: 1) iNOS:
Sense:
5'-CCCTTCCGAAGTTTCTGGCAGCAGC-3'

(SEQ ID NO: 2) Antisense:
5'-GGCTGTCAGAGCCTCGTGGCTTTGG-3'

(SEQ ID NO: 3) IL-1β:
Sense:
5'-CTCCATGAGCTTTGTACAAGG-3'

(SEQ ID NO: 4) Antisense:
5'-TGCTGATGTACCAGTTGGGG-3'

(SEQ ID NO: 5) MBP:
Sense:
5'-TGGAGAGATTCACCGAGGAGA-3'

(SEQ ID NO: 6) Antisense:
5'-TGAAGCTCGTCGGACTCTGAG-3'

(SEQ ID NO: 7) GAPDH:
Sense:
5'-GGTGAAGGTCGGTGTGAACG-3'

(SEQ ID NO: 8) Antisense:

5'-TTGGCTCCACCCTTCAAGTG-3'
```

The relative expression of each gene with respect to GAPDH was measured after scanning the bands with a Fluor Chem 8800 Imaging System (Alpha Innotech, San Leandro, Calif.).

Real-time PCR analysis was performed using the ABI-Prism7700 sequence detection system (Applied Biosystems, Foster City, Calif.). Briefly, reactions were performed in a 96-well optical reaction plates on cDNA equivalent to 50 ng DNase-digested RNA in a volume of 25 μL, containing 12.5 μL TaqMan Universal Master mix and optimized concentrations of FAM-labeled probe, forward and reverse primers following the manufacturer's protocol. All primers and FAM-labeled probes for mouse genes and GAPDH were obtained from Applied Biosystems. The mRNA expressions of respective genes were normalized to the level of GAPDH mRNA. Data were processed by the ABI Sequence Detection System 1.6 software and analyzed by ANOVA.

TGF-β ELISA.

Production of TGF-β in culture supernatant was monitored by ELISA using assay kit from eBioscience (San Diego, Calif.).

Flow Cytometry.

Two-color flow cytometry was performed as described previously. Briefly, $1\times10^6$ lymph node cells (LNC) or splenocytes suspended in flow staining buffer were incubated at 4° C. with appropriately diluted FITC-labeled Ab to CD4 for 30 min, washed, and re-suspended in fixation and permeabilization solution. Following incubation in dark for 30 min, cells were washed, blocked with test Fc block (anti-mouse CD16/32) in permeabilization buffer, and subsequently incubated with appropriately diluted PE-labeled Abs to Foxp3 at 4° C. in the dark. After incubation, the cell suspension was centrifuged, washed thrice, and re-suspended in flow staining buffer. The cells then were analyzed through FACS (BD Biosciences, San Jose, Calif.). Cells were gated based on morphological characteristics. Apoptotic and necrotic cells were not accepted for FACS analysis.

GTB Inhibits the Adoptive Transfer of EAE in Female SJL/J Mice.

The inventor induced RR-EAE in female SJL/J mice by adoptive transfer of MBP-primed T cells. These EAE mice were treated with different doses of GTB from 8 days post-transfer (dpt) when these mice exhibited a clinical score of 0.5 or higher. An additional group of mice was treated with vehicle (FIG. 1A). Even at a dose of 25 mg/kg body wt/d, GTB significantly inhibited clinical symptoms (FIG. 1A). On the other hand, at a dose of 50 mg/kg body wt/d, a dramatic inhibition of clinical symptoms was observed in acute as well as chronic phases of EAE (FIG. 1A). Vehicle (0.1% methyl cellulose) remained unable to inhibit the clinical symptoms of EAE (FIG. 1A), suggesting the specificity of the effect. However, at a dose of 100 mg/kg body wt/d, GTB was less potent than either 50 mg/kg body wt/d in suppressing clinical symptoms (FIG. 1A), suggesting that at higher dose, it may be toxic for EAE mice.

GTB Inhibits Clinical Symptoms and Disease Severity of EAE in Female PLP-TCR Transgenic Mice.

Next, the inventor examined if GTB treatment was also capable of suppressing the progression of EAE in female PLP-TCR transgenic (Tg) mice. As reported, immunization with low dose (10 μg/mouse) of PLP139-151 strongly induced clinical symptoms of EAE in female PLP-TCR Tg mice (FIG. 1B). EAE mice were treated with different doses of GTB from 8 days post immunization (dpi). An inhibitory effect of GTB on the clinical symptoms was clearly observed within a few days of treatment (FIG. 1B). Greater inhibition was observed on subsequent days of treatment, which was maintained throughout the duration of the experiment (FIG. 1B). In this case as well, maximum inhibition of EAE was observed at a dose of 50 mg/kg body wt/d of GTB (FIG. 1B). On the other hand, vehicle had no such inhibitory effect (FIG. 1B).

GTB Inhibits Chronic EAE in Male C57/BL6 Mice.

While female SJL/J mice are used to induce RR-EAE, chronic form of EAE is modeled in male C57/BL6 mice upon immunization with MOG35-55. Therefore, the inventor examined the efficacy of GTB in suppressing the disease process of chronic EAE. Similar to its effect on RR-EAE in female SJL/J mice and PLP-TCR Tg mice, GTB treatment also strongly inhibited the clinical symptoms of EAE in this chronic model (FIG. 1C). Again, vehicle had no effect on chronic EAE (FIG. 1C), suggesting the specificity of the effect.

GTB Treatment Inhibits the Generation of Encephalitogenic T Cells in Donor Mice.

T cells isolated from MBP-immunized donor mice are encephalitogenic and adoptive transfer of these T cells induces EAE in recipient mice. Therefore, the inventor investigated whether treatment of donor mice with GTB was capable of inhibiting the production of encephalitogenic T cells. In order to test this, donor mice were treated with GTB (50 mg/kg body wt/d) orally from the day of MBP immunization. T cells isolated from GTB-treated and untreated MBP-immunized donor mice were then adoptively transferred to recipient mice. The results showed that mice receiving MBP-primed T cells from GTB-treated donor mice exhibited significantly reduced clinical symptoms and disease severity compared to mice receiving MBP-primed T cells from either untreated donor mice or vehicle-treated donor mice (FIG. 2). These results suggest that GTB treatment inhibits the generation of encephalitogenic T cells in vivo in donor mice.

GTB Treatment Preserves the Integrity of Blood-Brain Barrier (BBB) and Blood-Spinal Cord Barrier (BSB) in Adoptively-Transferred EAE Mice.

Figure 3A:
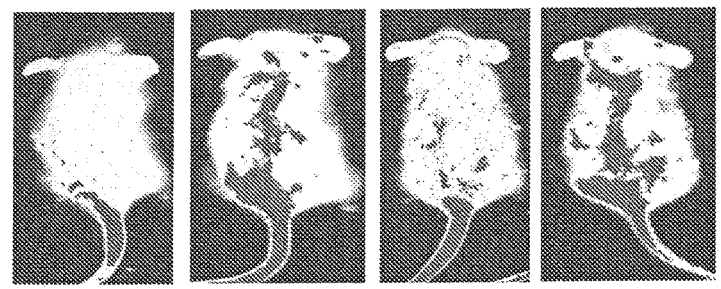

BBB and BSB are membranic structures that act primarily to protect the brain and the spinal cord, respectively from chemicals in the blood, while still allowing some essential molecules to enter. It is known that during active MS and EAE, BBB and BSB break down in a section of the brain and spinal cord, respectively due to widespread inflammation thereby allowing different blood molecules and toxins enter into the CNS. Therefore, the inventor investigated if GTB treatment modulated the integrity of BBB and BSB. The inventor injected an infrared dye (Alexa-680) via tail-vein and 2 h after the injection, live mice were scanned in an Odyssey infra-red scanner. As evidenced from FIG. 3A (first lane), infra-red signals were not visible on areas over the brain and the spinal cord in control HBSS-injected mice. On the other hand, in EAE mice, infra-red signals were detected on areas over the brain and the spinal cord (FIG. 3A; second column), suggesting possible breakdown of BBB and BSB. However, GTB treatment strongly inhibited the entry of infra-red dye into the CNS of EAE mice (FIG. 3A; compare lane 3 with lane 2). In contrast, vehicle treatment did not influence the entry of infra-red dye into the CNS of EAE mice as evidenced by the aligning of infra-red signals over spinal cord and brain (FIG. 3A; compare lane 4 with lane 2), suggesting the specificity of the effect.

Figure 3C:
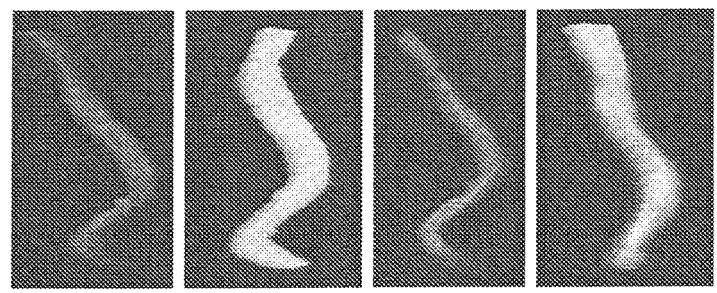
Figure 3C:
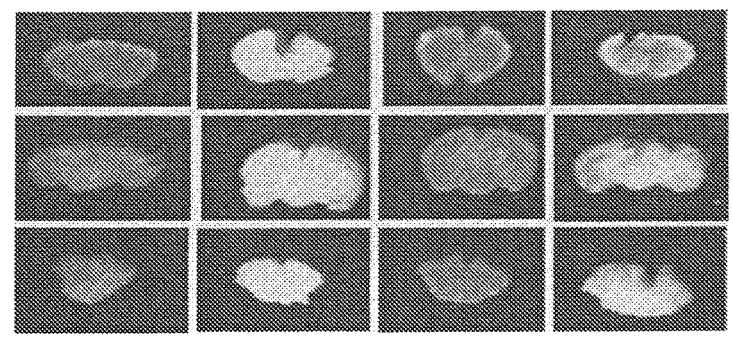
Figure 3D:
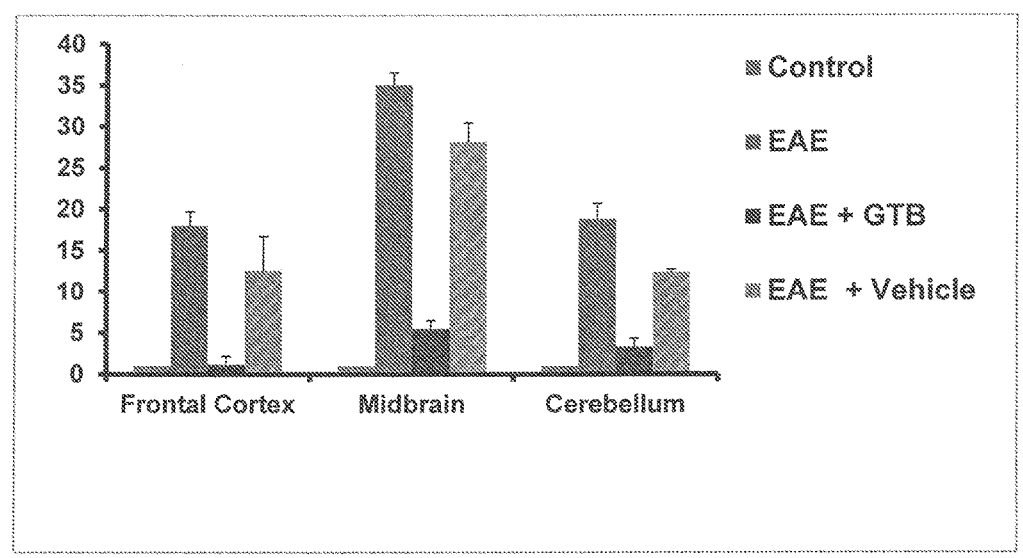
FIG. 3D depicts a graphical analysis of the data shown in FIGS. 3A-3C.

To confirm these results further, mice were sacrificed, and the spinal cord and different parts of the brain (frontal cortex, midbrain and cerebellum) were scanned for infra-red signals in Odyssey infra-red scanner. Consistent to live mice results, the inventor did not notice much infra-red signal in the spinal cord and different parts of the brain in control HBSS-treated mice (FIG. 3B-D; lane 1) but significant amount of infra-red dye was visible in CNS tissues of EAE mice (FIG. 3B-D; lane 2). Again, treatment of EAE mice by GTB markedly attenuated the entry of infra-red dye into the spinal cord and different parts of the brain (FIG. 3B-D; compare lane 3 with lane 2). Taken together, these results suggest that GTB treatment preserves the integrity of BBB and BSB in EAE mice. In FIG. 3C, the top row relates to the frontal cortex, the middle row relates to the midbrain, and the last row relates to the cerebellum. In FIG. 3D, the first column relates to the control, the second column relates to EAE, the third column relates to EAE+GTB, the fourth column relates to EAE+Vehicle, and the y-axis is density of infrared signal.

GTB Inhibits Infiltration of Mononuclear Cells, Inflammation and Demyelination in the Spinal Cord of EAE.

Figure 4A:
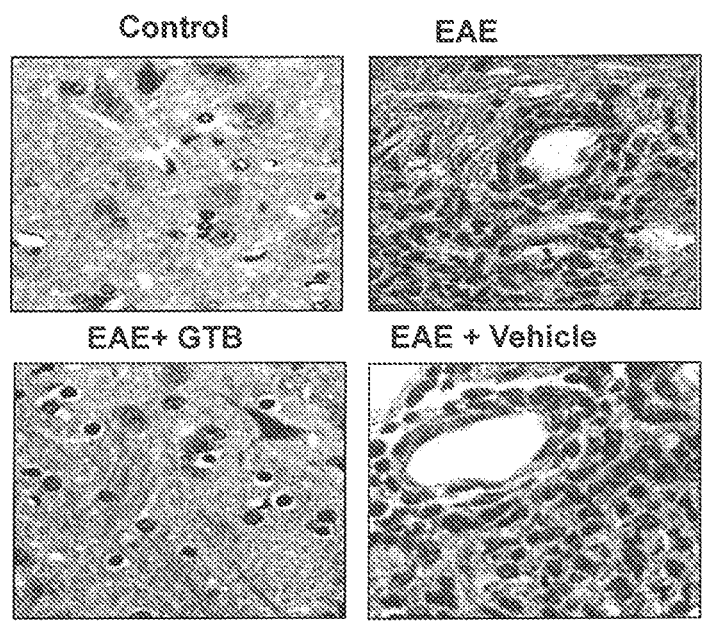
FIG. 4A depicts images indicating that GTB inhibits infiltration of mononuclear cells, inflammation and demyelination in the spinal cord of EAE.
Figures 4B, 4C:
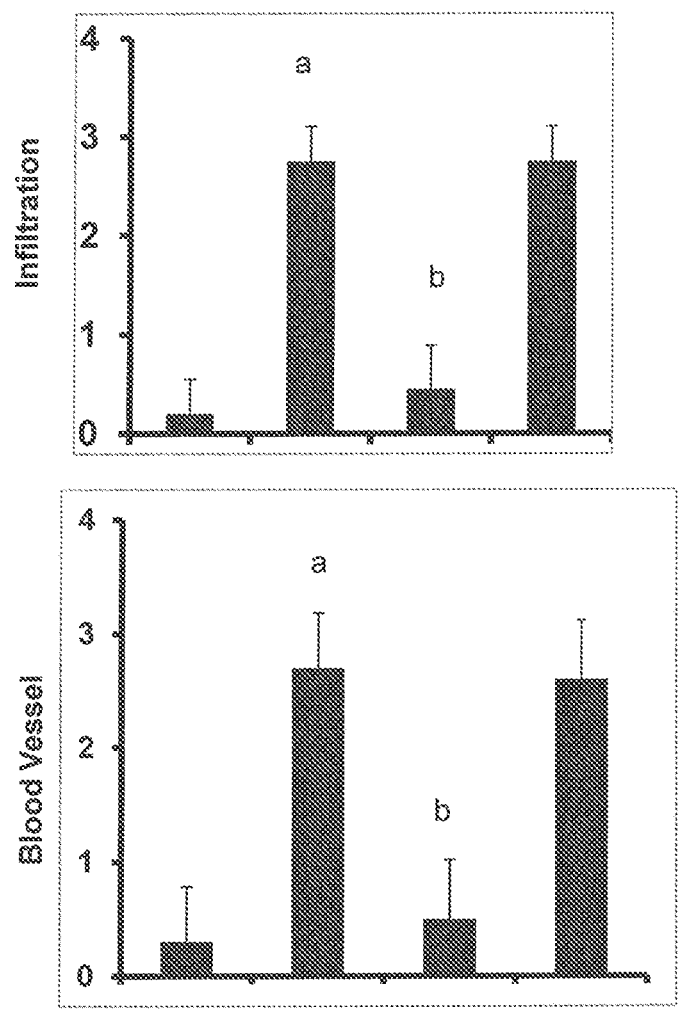
FIGS. 4B-4C depict graphical data indicating that GTB dramatically reduced infiltration and the appearance of cuffed vessels, respectively, in the spinal cord of EAE mice.

Infiltration of autoreactive T cells and associated mononuclear cells is a hallmark of EAE as well as MS. The inventor examined whether GTB treatment attenuated infiltration and inflammation in adoptively-transferred EAE mice. Mice receiving GTB from 8 dpt (onset of the acute phase) were sacrificed on 16 dpt. H & E staining showed widespread infiltration of inflammatory cells into the spinal cord (FIG. 4A) of EAE mice. On the other hand, GTB treatment markedly inhibited the infiltration of inflammatory cells into the spinal cord of EAE mice (FIG. 4A). In contrast, vehicle was unable to inhibit the infiltration of inflammatory cells (FIG. 4A). Quantitation of the relative level of inflammatory cells showed that GTB, but not vehicle, dramatically reduced infiltration (FIG. 4B) and the appearance of cuffed vessels (FIG. 4C) in spinal cord of EAE mice.

Next, the inventor examined whether GTB was capable of inhibiting the expression of proinflammatory molecules in the spinal cord of EAE mice. Marked expression of pro-inflammatory molecules like iNOS and IL-1β was observed in the spinal cord of untreated EAE mice compared to control mice (FIG. 4D-F). However, GTB treatment dramatically reduced the expression of these pro-inflammatory molecules in the spinal cord of EAE mice (FIG. 4D-F).

Figure 5A:
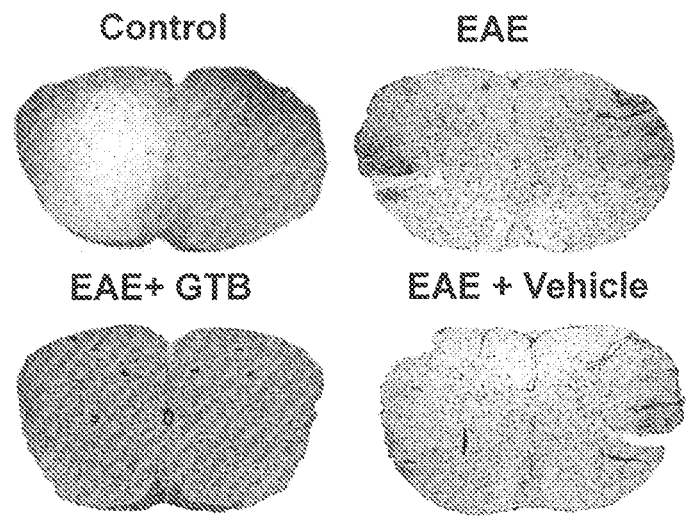
FIGS. 5A and 5B depict data indicating widespread demyelination zones in the white matter of a spinal cord and that GTB treatment remarkably restored myelin level in the spinal cord of EAE mice.
Figure 5B:
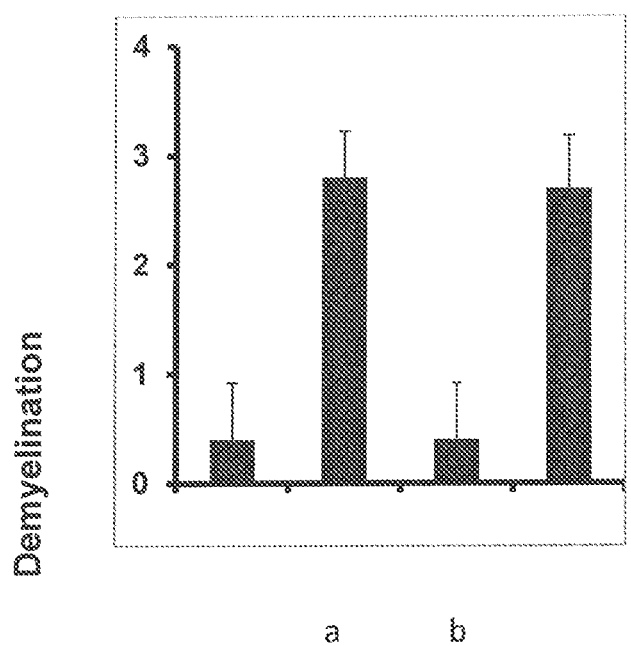
Figure 5C:
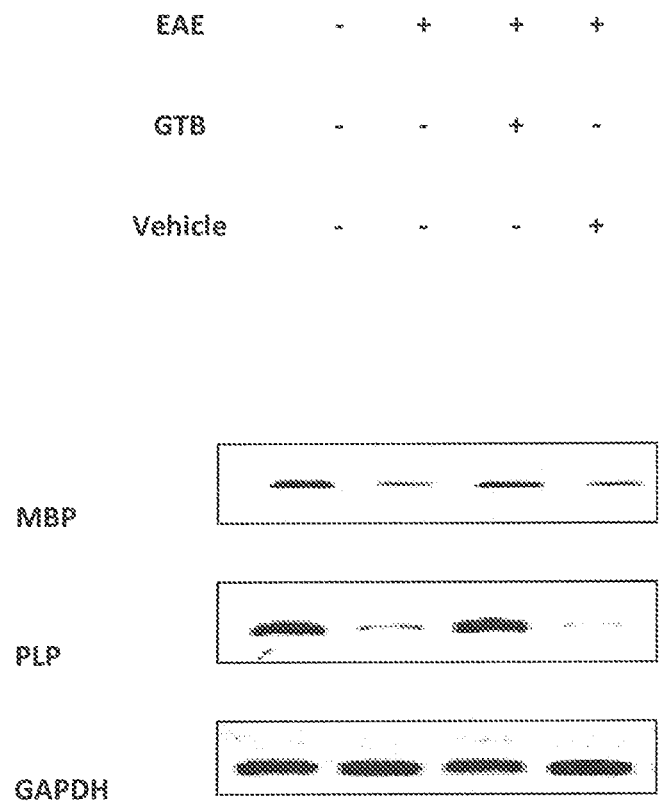

Demyelination is the most important pathological feature in MS, which is also modeled in EAE animals. Therefore, the inventor examined whether GTB protected EAE mice from demyelination. The inventor stained spinal cord sections by luxol fast blue (LFB) for myelin and observed widespread demyelination zones in the white matter (FIG. 5A-B). However, GTB treatment remarkably restored myelin level in the spinal cord of EAE mice (FIG. 5A-B). In contrast, vehicle was unable to restore myelin level in spinal cord of EAE mice (FIG. 5A-B). To confirm this finding, the inventor monitored the expression of three myelin genes, myelin basic protein (MBP) and proteolipid protein (PLP), and observed a marked loss of mRNA expression of these genes in the spinal cord of untreated EAE mice compared to control mice (FIG. 5C-E). However, significant restoration of myelin gene mRNA expression was observed in the spinal cord of EAE mice that were treated with GTB, but not vehicle (FIG. 5C-E).

GTB Treatment Protects Tregs in EAE Mice Via TGF-β.

Figure 6:
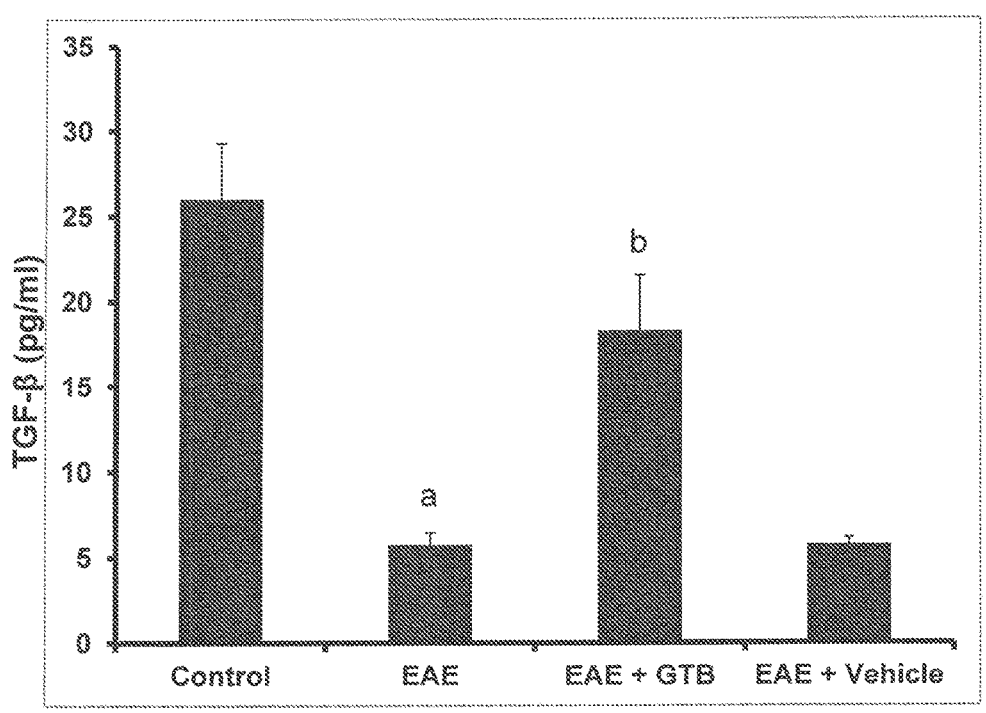
FIG. 6 depicts a graphical analysis showing a marked decrease in TGF-β in the serum of EAE mice as compared to control mice.

Because TGF-β is known to protect mice from EAE, the inventor examined the level of TGF-β in serum of GTB-treated and untreated EAE mice by ELISA. EAE mice receiving GTB or vehicle from 8 dpt were sacrificed on 16 dpt followed by analysis of TGF-β in serum. The inventor observed marked decrease in TGF-β in the serum of EAE mice as compared to control mice (FIG. 6). However, treatment of EAE mice with GTB, but not vehicle, protected TGF-β.

Figure 7:
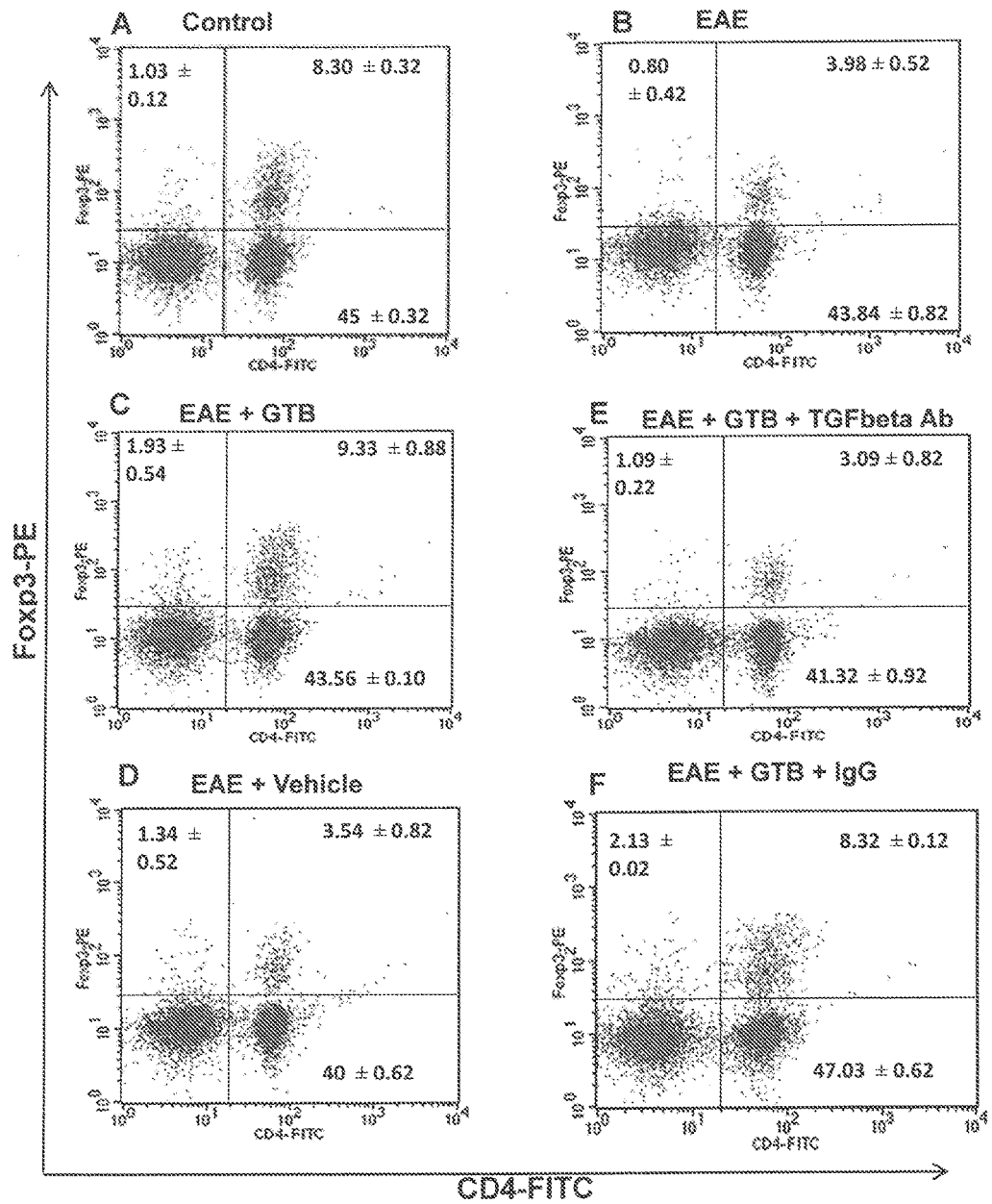
FIGS. 7A-7D depict images showing that treatment of EAE mice with GTB, but not vehicle, led to the increase in Foxp3+CD4+ population in splenocytes.
FIGS. 7E-7F depict images showing that co-treatment of EAE mice with TGF-β neutralizing antibodies abrogated GTB-mediated enrichment and/or protection of Foxp3+CD4+ population of T cells.

Since TGF-β is involved in the differentiation of non-Tregs into Tregs, the inventor monitored the status of Tregs in EAE mice. A major population of Tregs is characterized by a transcription factor FoxP3. During autoimmune insults, Tregs become both numerically and functionally defective. Therefore, as expected, the inventor observed significant reduction in Foxp3+CD4+ population of T cells in EAE splenocytes as evident from FACS dot plot (FIG. 7A-B). However, similar to the increase in TGF-β, treatment of EAE mice with GTB, but not vehicle, led to the increase in Foxp3+CD4+ population in splenocytes (FIG. 7A-D).

Next, to understand whether GTB enriches Tregs in EAE mice via TGF-β, the inventor employed TGF-β neutralizing antibodies and EAE mice were treated with both GTB and TGF-β neutralizing antibodies. Interestingly, co-treatment of EAE mice with TGF-β neutralizing antibodies abrogated GTB-mediated enrichment and/or protection of Foxp3+ CD4+ population of T cells (FIG. 7A-F). On the other hand, control IgG had no such abrogating effect, suggesting the specificity of the effect. These results clearly show that GTB treatment protects Tregs in EAE mice via TGF-β.

GTB Suppresses EAE in Mice Via TGF-β.

Figure 8:
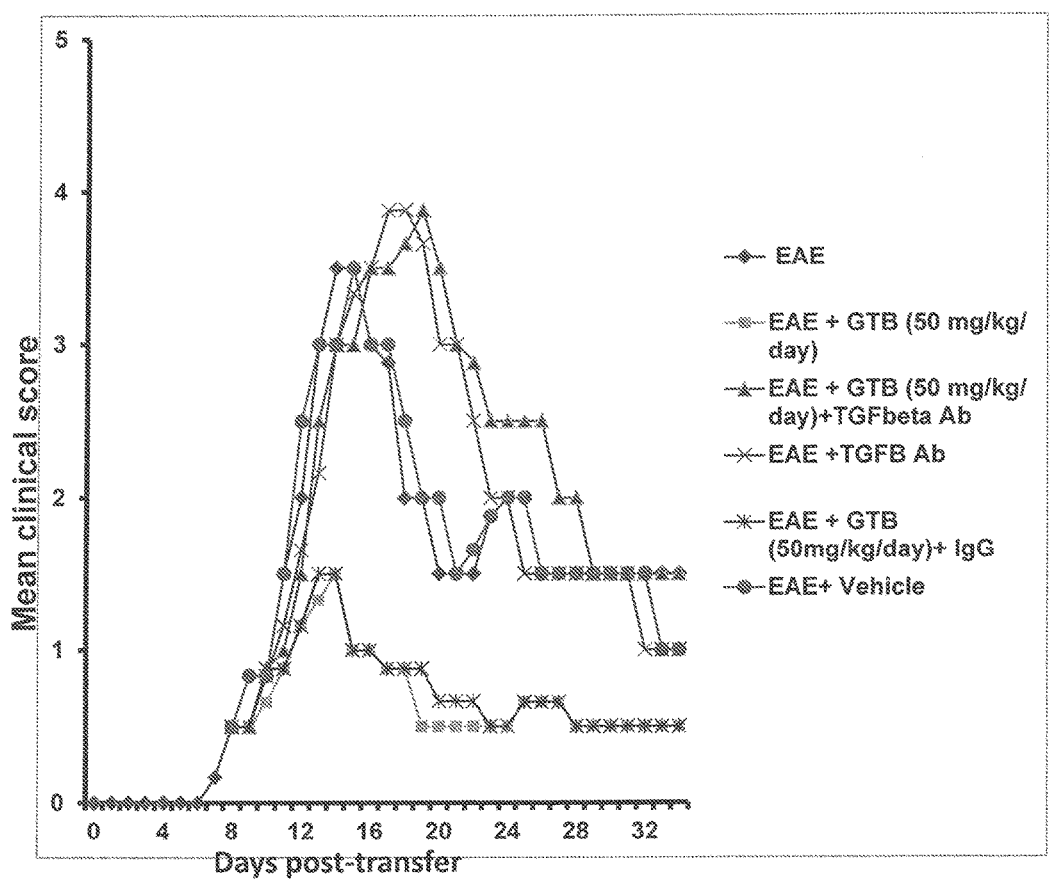
FIG. 8 depicts a graphical analysis of data showing that GTB treatment ameliorated clinical symptoms of adoptively-transferred RR-EAE but functional blocking anti-TGF-β antibody almost completely abrogated the GTB-mediated protective effect on EAE mice.

Next, in order to test the functional significance of GTB-mediated increase in TGF-β further, the inventor examined whether GTB protected mice from clinical symptoms of EAE via TGF-β. Therefore, during GTB treatment, the function of TGF-β was blocked in vivo in EAE mice by anti-TGF-β neutralizing antibody. As evident from FIG. 8, GTB treatment ameliorated clinical symptoms of adoptively-transferred RR-EAE. However, functional blocking anti-TGF-β antibody almost completely abrogated the GTB-mediated protective effect on EAE mice (FIG. 8). This result was specific as control IgG had no such effect (FIG. 8). Together, these results suggest that GTB protects EAE via TGF-β.

In summary, oral feeding of GTB suppressed clinical symptoms of adoptively-transferred relapsing-remitting (RR) EAE in recipient mice and suppressed the generation of encephalitogenic T cells in donor mice. GTB also inhibited clinical symptoms of RR-EAE in female PLP-TCR transgenic mice and chronic EAE in male C57/BL6 mice. Dose-dependent study showed that GTB at a dose of 25 mg/kg body wt/d or higher significantly suppressed clinical symptoms of EAE in mice. Accordingly, GTB also inhibited perivascular cuffing, maintained the integrity of blood-brain barrier and blood-spinal cord barrier, suppressed inflammation, normalized the expression of myelin genes, and blocked demyelination in the CNS of EAE mice. Interestingly, GTB treatment upregulated TGF-β and regulatory T cells (Tregs). Furthermore, it has been demonstrated that blocking of TGF-β by neutralizing antibodies abrogated GTB-mediated protection of Tregs and EAE. Taken together, these results suggest that oral administration of GTB may be beneficial in MS patients.

Experiments were also carried out testing GTB in connection with Parkinson's disease (PD).

Animals and MPTP Intoxication.

Six- to eight-week old C57BL/6 mice were purchased from Harlan (Indianapolis, Ind.). For acute MPTP intoxication, mice received four intraperitoneal (i.p.) injections of MPTP-HCl (18 mg/kg of free base; Sigma Chemical Co., St. Louis, Mo.) in saline at 2-h intervals. Control animals received only saline.

Glyceryl Tribenzoate (GTB) Treatment.

GTB was mixed in 0.5% methylcellulose (MC) and from 3 h after the last injection of MPTP, mice were gavaged 100 µL GTB-mixed MC once daily using gavage needle. Therefore, control MPTP mice received only MC as vehicle.

Western Blot Analysis.

Immunoblot analysis for DJ-1 and TH was carried out. Briefly, cell homogenates were electrophoresed, proteins were transferred onto a nitrocellulose membrane, and bands were visualized with an Odyssey infrared scanner after immunolabeling with respective primary antibodies followed by infra-red fluorophore-tagged secondary antibody (Invitrogen).

HPLC Analyses.

Striatal level of dopamine was quantified in Complete Stand-Alone HPLC-ECD System EiCOMHTEC-500 (JM Science Inc., Grand Island, N.Y.). Briefly, mice were sacrificed by cervical dislocation after 7 days of MPTP intoxication and their striata were collected and immediately frozen in dry ice and stored at −80° C. until analysis. On the day of the analysis, tissues were sonicated in 0.2M perchloric acid containing isoproterenol and resulting homogenates were centrifuged at 20,000×g for 15 min at 4 C. After pH adjustment and filtration, 10 µl of supernatant was injected onto an Eicompak SC-3ODS column (Complete Stand-Alone HPLC-ECD System EiCOMHTEC-500 from JM Science Inc., Grand Island, N.Y.) and analyzed following the manufacturer's protocol.

Figure 9:
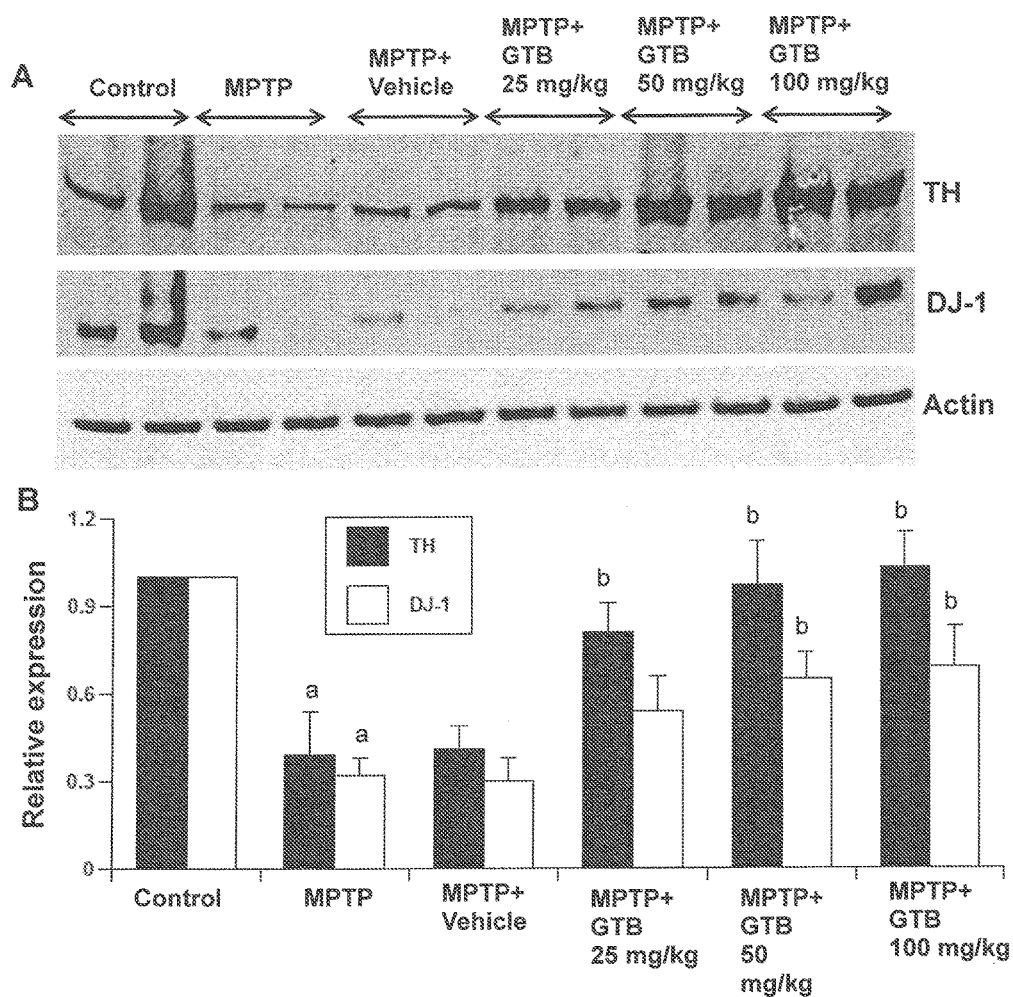
FIGS. 9A-9B depict data showing MPTP intoxication decreased the level of DJ-1 in vivo in the nigra but oral treatment of MPTP-intoxicated mice with GTB, but not vehicle, protected DJ-1 in the nigra.

Upregulation and/or maintenance of PD-related beneficial protein such as DJ-1 in the nigra during neurodegenerative insults may have therapeutic efficacy in PD. As expected, MPTP intoxication decreased the level of DJ-1 in vivo in the nigra (FIG. 9A-B). However, oral treatment of MPTP-intoxicated mice with GTB, but not vehicle (0.1% methyl cellulose) protected DJ-1 in the nigra (FIG. 9A-B). Protective effect of GTB was dose-dependent and the maximum protection was seen at a dose of 50 or 100 mg/kg body wt/d (FIG. 9A-B).

Since GTB protected DJ-1 in the nigra of MPTP-intoxicated mice, next, the inventor investigated if DJ-1 protected the nigrostriatum from MPTP insult. Tyrosine hydroxylase (TH), the key enzyme responsible for the production of dopamine, is present in dopaminergic neurons. MPTP-intoxication led to approximately 60% loss of nigral TH (FIG. 9A-B) compared with saline-injected controls. However, GTB protected nigral TH in a dose-dependent manner (FIG. 9A-B). Although GTB-mediated protection was evident at a dose of 25 mg/kg body wt/d, maximum protection of nigral TH was observed at a dose of 50 or 100 mg/kg body wt/d (FIG. 9A-B).

Figure 10:
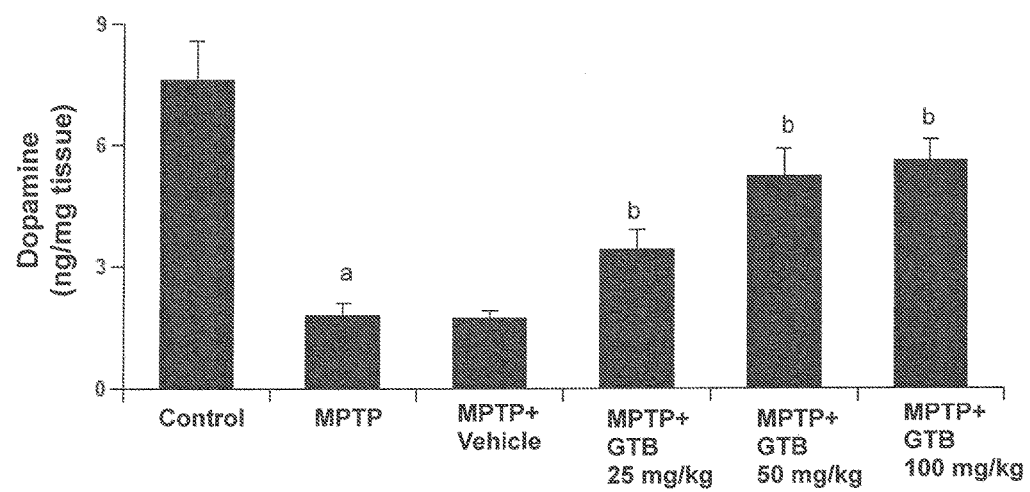
FIG. 10 depicts a graphical analysis indicating that MPTP intoxication led to about 75% decrease in striatal DA compared to striata of saline-injected control mice but GTB treatment dose-dependently protected dopamine in vivo in the striatum of MPTP-intoxicated mice.

Next, to determine whether GTB protects against biochemical deficits caused by MPTP, the inventor quantified levels of dopamine (DA) in the striata 7 days after the MPTP treatment. As evident from FIG. 10, MPTP intoxication led to about 75% decrease in striatal DA compared to striata of saline-injected control mice. In contrast, GTB treatment dose-dependently protected dopamine in vivo in the striatum of MPTP-intoxicated mice (FIG. 10). In this case as well, maximum protection of striatal dopamine was observed at a dose of 50 or 100 mg/kg body wt/d of GTB (FIG. 10). Animals that received GTB at a dose of 50 mg/kg body wt/d showed only 25% decrease in striatal dopamine (FIG. 10).

The inventor did not notice any drug related side effect (e.g. hair loss, weight loss, untoward infection etc.) in any of the mice used during the course of the study, suggesting that GTB may not exhibit any side effects.

In summary, the inventor demonstrated that GTB protects DJ-1 and TH in the nigra and preserves dopamine in the striatum in MPTP mouse model of PD. These results highlight a novel neuroprotective role of GTB and suggest that this indirect food additive may be explored for therapeutic intervention in PD.

In the future, the inventor will determine if tribenzoin treatment improves motor functions in MPTP-intoxicated mice. Male C57/BL6 mice will be intoxicated with MPTP and from 6 hours after the last injection of MPTP, the mice will receive tribenzoin (25 and 50 mg/kg body weight/day) via gavage. The mice will be tested for motor functions (A, rotorod; B, movement time; C, number of movements; D, rest time; E, horizontal activity; F, total distance; G, rearing; and H, stereotypy) 7 days after the last injection of MPTP. The data will be means±SEM of six mice per group.

In the future, the inventor will delineate if tribenzoin treatment protects hippocampal neurons and improves memory and learning in 5XFAD mice, an animal model for Alzheimer's disease. Briefly, six-month old male 5XFAD mice will receive tribenzoin (25 and 50 mg/kg body weight/day) via gavage. After 30 d of treatment, mice will be tested for Barnes maze, T maze and Novel Object Recognition. Conclusion will be drawn from analysis of at least six mice per group. Hippocampal sections will be also double-labeled for NeuN (marker of neuron) and TUNEL (marker of apoptosis). Results will represent analysis of two hippocampal sections of each of six mice per group.

The inventor will also confirm the efficacy of tribenzoin in urea cycle disorders. Hyperammonemia is a condition associated with all urea cycle disorders. Therefore, a mouse model of hyperammonemia will be created by feeding mice a standard diet supplemented with ammonium acetate (20% w/w) for 3 months. Then, mice will be treated with different doses of tribenzoin (about 100, 200, or 300 mg/kg body weight/day) via gavage for 30 days. After treatment, the levels of ammonia, glutamine, urea, and glycine in serum will be investigated.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a compound" is intended to include "at least one compound" or "one or more compounds."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method for inhibiting the progression of a urea cycle disorder comprising administering to a patient in need thereof an effective amount of a pharmaceutical composition comprising glyceryl tribenzoate and/or glyceryl dibenzoate.

2. The method of claim 1, wherein the pharmaceutical composition is administered to the patient one time per day.

3. The method of claim 1, wherein the effective amount is from about 3 grams to about 10 grams per day, based on a 50 kg patient.

4. The method of claim 1, wherein the pharmaceutical composition is formulated together with a pharmaceutically acceptable carrier or excipient.

5. The method of claim 1, wherein the pharmaceutical composition is administered orally.

6. The method of claim 1, wherein the urea cycle disorder is selected from the group consisting of N-acetylglutamate synthase deficiency, Carbamoyl Phosphate Synthetase 1 deficiency, Ornithine transcarbamoylase deficiency, Argininosuccinate synthase deficiency, argininosuccinate lyase deficiency, Arginase 1 deficiency, and any combination thereof.

7. A method for inhibiting the progression of a neurodegenerative disorder comprising administering to a patient in need thereof an effective amount of a pharmaceutical composition comprising glyceryl tribenzoate and/or glyceryl dibenzoate, wherein the neurodegenerative disorder is selected from the group consisting of multiple sclerosis, Parkinson's disease, Alzheimer's disease, and depression.

8. The method of claim 7, wherein the pharmaceutical composition is administered to the patient one time per day.

9. The method of claim 7, wherein the effective amount is from about 1 gram to about 5 grams per day, based on a 50 kg patient.

10. The method of claim 7, wherein the effective amount is about 1.25 grams per day, based on a 50 kg patient.

11. The method of claim 7, wherein the pharmaceutical composition is formulated together with a pharmaceutically acceptable carrier or excipient.

12. The method of claim 7, wherein the pharmaceutical composition is administered orally.

13. A process of preparing a pharmaceutical composition for the treatment of a urea cycle disorder, comprising mixing a glyceryl tribenzoate and/or a glyceryl dibenzoate compound together with a pharmaceutically acceptable carrier or excipient.

14. The method of claim 13, wherein the urea cycle disorder is selected from the group consisting of N-acetylglutamate synthase deficiency, Carbamoyl Phosphate Synthetase 1 deficiency, Ornithine transcarbamoylase deficiency, Argininosuccinate synthase deficiency, argininosuccinate lyase deficiency, Arginase 1 deficiency, and any combination thereof.

15. A process of preparing a pharmaceutical composition for the treatment of a neurodegenerative disorder, comprising mixing a glyceryl tribenzoate and/or a glyceryl dibenzoate compound together with a pharmaceutically acceptable carrier or excipient, wherein the neurodegenerative disorder is selected from the group consisting of multiple sclerosis, Parkinson's disease, Alzheimer's disease, and depression.

* * * * *

SEQUENCE LISTING

```
<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
cccttccgaa gtttctggca gcagc                                        25

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
ggctgtcaga gcctcgtggc tttgg                                        25

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
ctccatgagc tttgtacaag g                                            21

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
tgctgatgta ccagttgggg                                              20

<210> SEQ ID NO 5
<211> LENGTH: 21
```

```
-continued

<212> TYPE: DNA
<213> ORGANISM: Artificial Sequence
<220> FEATURE:
<223> OTHER INFORMATION: Primer

<400> SEQUENCE: 5
tggagagatt caccgaggag a                                              21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
tgaagctcgt cggactctga g                                              21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ggtgaaggtc ggtgtgaacg                                                20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ttggctccac ccttcaagtg                                                20
```